United States Patent [19]

Mabille

[11] Patent Number: 4,492,575
[45] Date of Patent: Jan. 8, 1985

[54] DENTAL PROPHYLACTIC APPARATUS

[75] Inventor: Pierre Mabille, Le Sentier, Switzerland

[73] Assignee: Electro Medical Systems, S.A., Le Sentier, Switzerland

[21] Appl. No.: 489,122

[22] Filed: Apr. 27, 1983

[30] Foreign Application Priority Data

Jun. 22, 1982 [FR] France ................ 82 10920

[51] Int. Cl.³ .............................. A61C 3/02
[52] U.S. Cl. ........................ 433/88; 251/5; 251/7; 51/436; 51/438; 51/439
[58] Field of Search ............ 433/88, 125, 216; 51/426, 427, 428, 436, 437, 438, 439; 251/4, 5, 7, 8, 63.4; 222/630, 173; 118/308

[56] References Cited

U.S. PATENT DOCUMENTS

| | | | |
|---|---|---|---|
| 554,300 | 2/1896 | Parker | 51/436 |
| 2,409,768 | 10/1946 | Lavett et al. | 251/5 |
| 2,588,212 | 3/1952 | Custer | 251/5 |
| 2,792,971 | 5/1957 | Kaiser | 222/630 |
| 2,827,919 | 3/1958 | Rice et al. | 251/5 |
| 2,899,106 | 8/1959 | Weinert | 222/82 |
| 2,901,867 | 9/1959 | Bolton et al. | 51/426 |
| 2,985,050 | 5/1961 | Schwacha | 51/439 |
| 3,089,285 | 5/1963 | Moore | 51/438 |
| 3,158,966 | 12/1964 | Mead | 51/426 |
| 3,491,983 | 1/1970 | Van Damme et al. | 251/5 |
| 3,815,286 | 6/1974 | Piet | 51/427 |
| 3,866,357 | 2/1975 | Callahan et al. | 51/438 |
| 3,882,638 | 5/1975 | Black | 51/428 |
| 3,882,899 | 5/1975 | Ginsberg et al. | 251/5 |
| 4,090,334 | 5/1978 | Kurowski et al. | 51/427 |
| 4,174,571 | 11/1979 | Gallant | 433/216 |

Primary Examiner—John J. Wilson
Attorney, Agent, or Firm—Hill, Van Santen, Steadman & Simpson

[57] ABSTRACT

A prophylactic apparatus for cleaning teeth with a flow of air containing powder particles and a flow of water characterized by a first air line extending from a source of pressurized air through at least one filter to a mixing device, a first control device arranged in the first air line for controlling the flow therethrough, the mixing device having a chamber for receiving powder to be fluidized and mixed with air to form an air laden with powder particles, a nozzle connected to the first air line disposed above the level of the particles, a discharge opening disposed above the level of the particles in the chamber connected to a second air line extending to a second nozzle opening, a second control arrangement for controlling the flow of air laden with powder particles in the second air line and an arrangement for unclogging each filter by creating a backflow from at least the chamber of the mixing device and a portion of the first line. Preferably, the first control arrangement comprises a valve which enables selectively connecting the source of pressurized air to the first line and venting the first line to the atmosphere to create the reverse flow for unclogging the filters.

18 Claims, 7 Drawing Figures 4,492,575

DENTAL PROPHYLACTIC APPARATUS

BACKGROUND OF THE INVENTION

The present invention is directed to a prophylactic apparatus for cleaning teeth with both a flow of air containing powder particles and a flow of water. The apparatus includes a hand piece having a nozzle opening for both the air that contains the abrasive particles and also an opening for a fluid such as water and these nozzle openings are connected to the respective feed lines for the air laden with abrasive particles and for the water.

Several devices are known in which a cleaning of the teeth is obtained by utilizing a hand piece which has a nozzle through which a jet of gaseous medium such as air containing abrasive particles is directed onto the surface of the teeth. The hand piece will also have a nozzle for directing a liquid jet such as a water jet which can be applied in the immediate vicinity of the surface of the tooth or immediately at the point on the surface of the tooth in which the jet of abrasive powder is directed.

However, the employment of these known apparatuses have several difficulties and disadvantages which require high maintenance costs. In particular, the known devices utilize a structure for obtaining a mixture of the air and powder which does not always permit the obtaining of a uniform distribution of the powder in the gaseous jet. Moreover, the known devices tend to become clogged and require daily cleaning after each stoppage of the apparatus. Finally, the known apparatuses on the whole are very heavy and cumbersome to use.

SUMMARY OF THE INVENTION

The present invention is directed to providing a dental prophylactic apparatus which is compact in structure, easy to utilize, is effective and requires a reduced maintenance due to the automatic cleansing after each use.

These objects are achieved with a dental prophylactic apparatus for cleaning teeth with a flow of air containing powder particles, the apparatus comprising a hand piece with a first nozzle opening and a second nozzle opening, a water line with a valve means extending from a source of water and being connected to the first nozzle opening, a first air line extending from a source of pressurized air to a mixing device, a first control means disposed in the first air line for controlling flow of air therethrough, the first air line between the first control means and the mixing device having a section containing at least one air filter, the mixing device having a chamber for receiving powder to be fluidized and mixed with air to form the air laden with powder particles, the mixing device having a jet nozzle disposed above the level of powder in the chamber connected to the section of the first air line and a discharge opening disposed above the level of the powder in the chamber connected to a second air line extending to the second nozzle opening of the hand piece, second control means for controlling the flow of air laden with powder particles in the second air line and means for unclogging each filter by creating a reversed flow of air from the second line through the chamber, the jet nozzle, the section of the first line and through each filter.

Preferably, the second control means includes a pinch valve for collapsing the second air line in response to the application of an air pressure. To apply the air pressure on the pinch valve, a third air line having a third control means extends from the pinch valve to the first air line at a point between the first control means and the section with filters. Preferably, the first control means and the means for unclogging each filter are formed by a solenoid valve which has one position connecting the source of air to the section of the first line passing through the filters and a second position blocking flow from the air source and venting the section of the first line and the filters to the atmosphere to obtain the reverse flow from the mixing device. When the apparatus is turned on, the solenoid valve is normally held in a position with the source being connected to the section of the first air line and when the device is turned off, the valve then goes to a second position venting the section of the first air line to the atmosphere while blocking flow from the air source.

According to another feature of the invention, the mixing device has the jet nozzle provided with two jets which are directed toward the base of the chamber or receptacle and are spaced above the level of the powder particles contained in the receptacle or chamber. The jet nozzle with the two jets is approximately adjacent a lateral wall of the receptacle and in an eccentric fashion relative to the axis of the receptacle. The discharge opening or exit orifice is located approximately 90° from the location of the jet nozzle adjacent an upper portion of the chamber for receiving the air containing the fluidized particles created by directing the flow of air through the jets at the powder.

The pinch valve of the second control means as mentioned hereinabove is actuated by an application of gas under pressure to a chamber. Preferably, the pinch valve construction comprises a chamber forming a cylinder with a base receiving a first piston which chamber is in communication with a source of pressurized medium such as air that moves the piston toward the base against a stop or abutment surface. The first piston carries an intermediate member such as a second piston received in a bore. The first piston is urged away from an abutment surface against the pressure in the chamber by springs and the second piston is biased by a spring means in the bore or passage toward the base. The first piston is designed so that the second air line or tube is received in a groove or passageway as the piston engages the stop which is the base. Thus, when air pressure is applied to the first piston, it is moved from a retracted position against a stop and the second piston is urged by its baising means to collapse the tube. The pressure applied to collapse and close the tube is exerted by the second piston and is always the same regardless of the particular air pressure applied to move the first piston against the stop. Thus, there is no problem of exerting too much pressure to collapse the tube and of possibly damaging the material of the tube by an overexertion of the pinching force.

Preferably, the apparatus includes a case having a support plate or partition which is mounted in the case in a pivotal fashion. Preferably, the filter and mixing device are secured on the support plate and if one or more of the outer panels of the case are removed the support plate can be pivoted to gain access to these devices.

The mixing device in the preferred embodiment preferably has an upper stopper or cap, which extends through an upper panel of the case. Thus, access to the chamber which receives the powder can be obtained by removing the stopper or upper cap.

Preferably, the hand piece which has the first and second nozzle openings has these nozzle openings provided in a nozzle head or portion with the second nozzle opening through which the air and powder mixture is discharged being on the axis of the head and the first nozzle opening being an annular opening surrounding the second opening. The annular opening of the first nozzle opening is connected to a chamber which in turn is connected to the water line so that the air and powder mixture is discharged from the second nozzle opening as a jet with the water being discharged as an annular curtain around the power and air jet.

DESCRIPTION OF THE PREFERRED EMBODIMENTS

Figure 1:
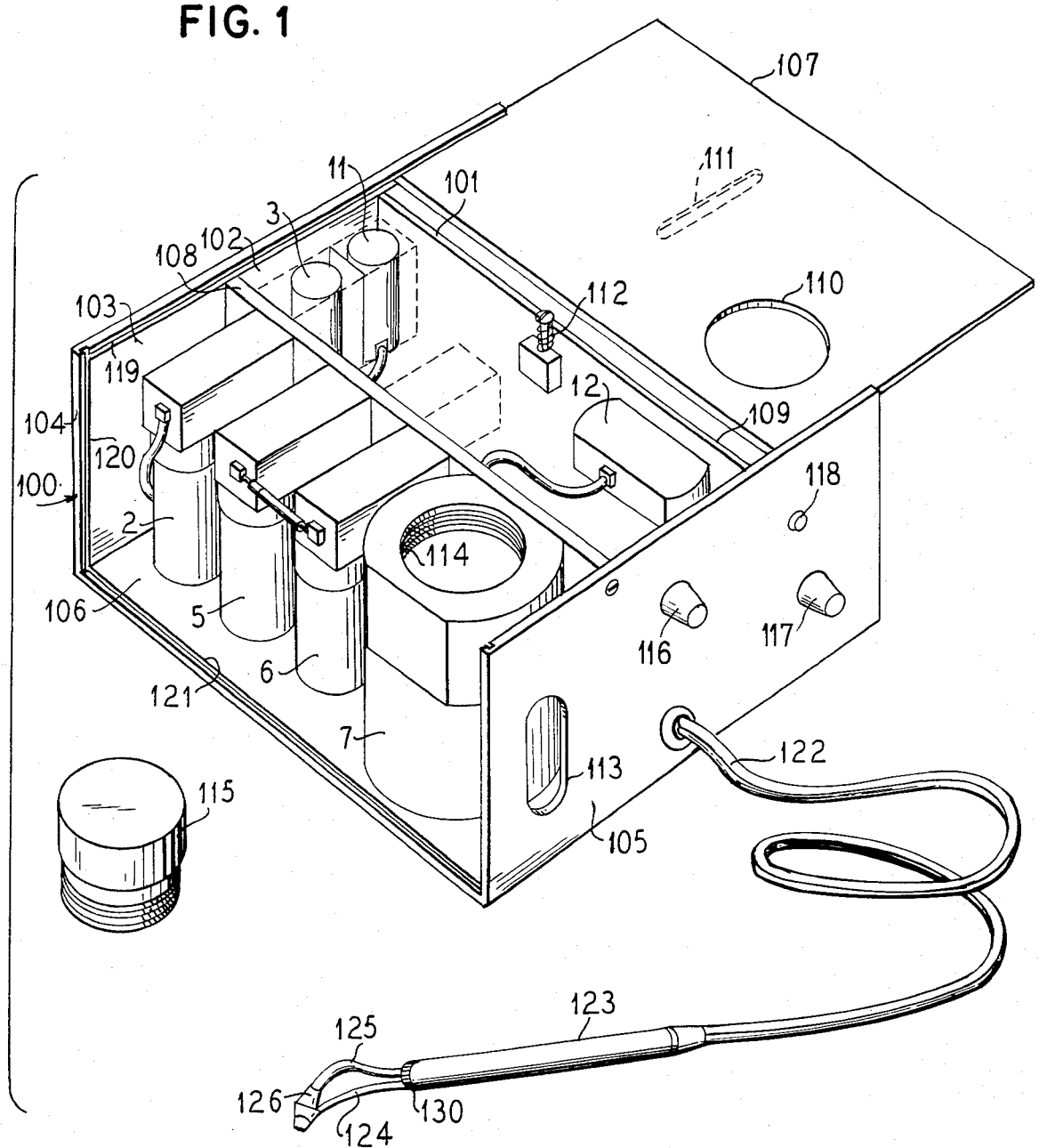
FIG. 1 is a perspective view with portions removed of the apparatus in accordance with the present invention.
Figure 6:
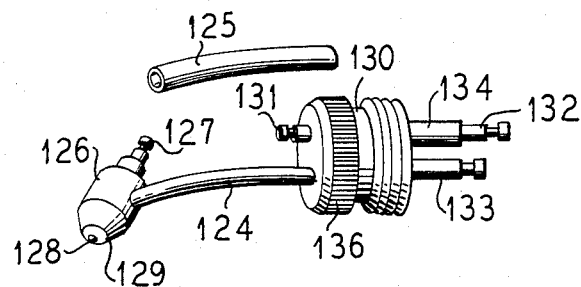
FIG. 6 is an enlarged exploded view of an end of the hand piece of the device of FIG. 1.

The principles of the present invention are particularly useful in a prophylactic apparatus generally indicated at 100 in FIG. 1. The apparatus 100 has a first filter 2, a first control means 3, an air regulator 4 (see FIG. 2), two additional filters 5 and 6, a mixing device 7 and second control means which include a pitch valve 12 and a third air control means 11. In addition, the apparatus 100 has a hand piece 123 which terminates in a nozzle head 126 which, as best illustrated in FIG. 6, has a first nozzle opening 129 and a second nozzle opening 128.

Figure 2:
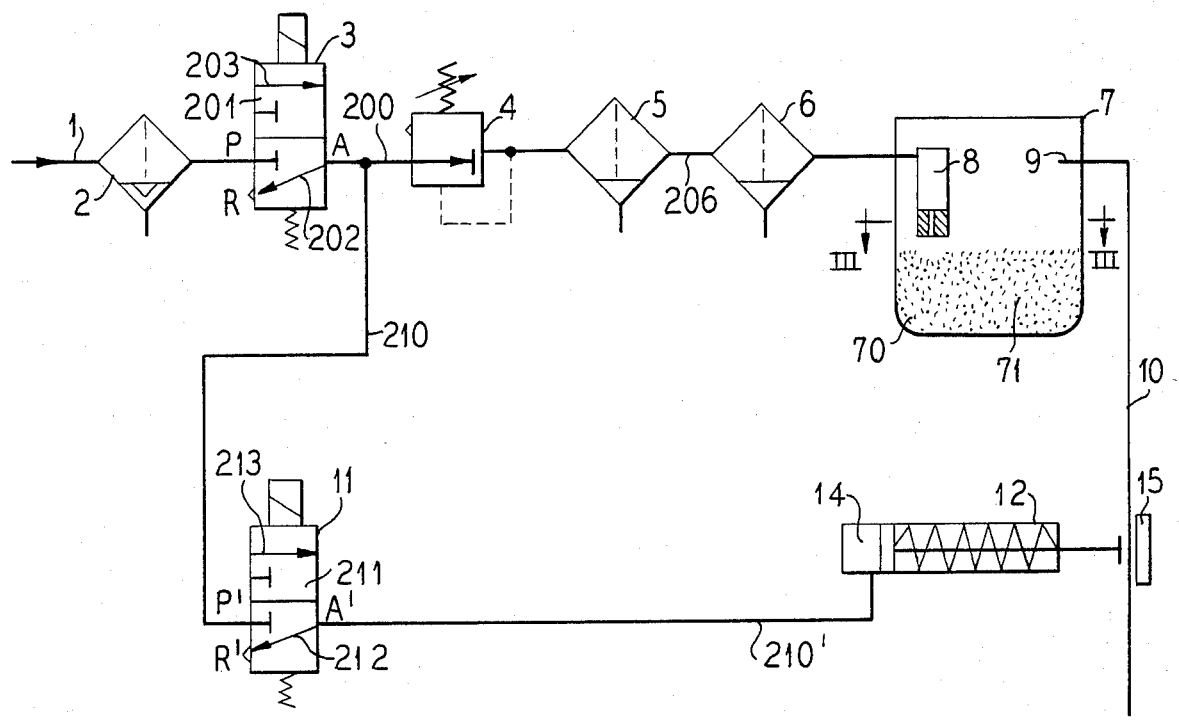
FIG. 2 is a general pneumatic plan for the apparatus of FIG. 1.

As best illustrated in the pneumatic plan of FIG. 2, pressurized air from a source at an air pressure of 3 to 10 kg/cm$^3$ is provided on an inlet socket or hose 1. This air then passes through an automatic powder filter 2 which has an outlet connected to a housing of the first control means 3. As illustrated, the first control means is a solenoid valve which has an incoming or first port P connected to the source of air, an outlet or second port A, which is connected to a first air line 200 and also an outlet or third port R which is connected to the atmosphere. A valve member 201 has an arrangement with a passageway 202 and also a passageway 203. In the illustrated position which is the deenergized position, the valve member has a passageway 202 connecting the second port A to the third port R and the first port P is blocked. In the other position which is obtained when the valve is actuated by closing the main circuit or switch of the apparatus, the passage 203 will connect the first port P to the second port A so that the air line 200 is charged with air from the source or socket 1 connected to the air source.

The line 200 preferably extends through a pressure regulator 4 whose output then passes through at least one filter and has illustrated two filters 5 and 6 which are arranged in series in a section 206 of the line 200. The section 206 terminates in a jet nozzle 8, which is arranged in a mixing device 7. As illustrated, the mixing device 7 has a chamber or receptacle 70, which receives powder or particles 71. The jet nozzle 8, which will be discussed in greater detail, is positioned to project the air in a line 200 downward on the powder 71 to cause a fluidizing and mixing of the powder with the air which is then removed through an outlet opening or exit port 9 which is connected to a second air line 10.

As illustrated, the second air line 10 passes through a pinch valve 12 of a second control means which will be discussed in greater detail. The second control means also includes a third air control means 11 which controls the flow of pressurized air in a line 210 which extends from the first line 200 and has a section 210' that discharges into a chamber 14 of the pinch valve 12.

As illustrated, the third control means 11 is similar to the control means 3 and has a member 211 having passages 212 and 213 and a housing with a first port P', a second part A' and a third port R'. When the member 211 is in the illustrated deenergized position, the passage 212 connects the second part A' to the third port R' to vent chamber 14 and when the member 211 is in the energized position, the passage 213 connects ports P' and A' together. When in the energized position with the passage 213 connecting the port P' and A', air under pressure passes through the air line 210 into section 210' to the chamber 14 to act on a piston to cause the pinch valve 12 to pinch the hose 10 closed to prevent the passage of air and the entrained particles of the powder to the hand piece 123. The solenoid valve is controlled by a switch such as a foot switch (not illustrated) which opens the circuit to cause the member 211 to move to the illustrated position. When the switch is opened, the valve will move to the position with the passageway 212 connecting the chamber 14 to the atmosphere through the exhaust or third port R'. This results in a release of the pinching of the second line 10 so that the flow of pressurized air through the nozzle 8 will cause a fluidization of the powder which powder will mix with the other air and be discharged through the exit opening or port 9 into the second air line 10 for discharge through a nozzle opening such as 128 in FIG. 6. When the pinch valve 12 releases the line 10 as mentioned hereinabove, a drainage of the gas under pressure in the receptacle 70 will occur. The air that flows out of the port 9 allows the discharge through the nozzle 8 to cause a fluidizing and therefore produce a flow of air and particles of powder. When the solenoid valve is actuated to shift it to the position connecting the port P' to the port A' to allow applying air under pressure to the chamber 14, the conduit or line 10 is then compressed or collapsed to prevent passage of air and any powder. With the prevention of passage of any air or powder past the pinch valve 12, flow through the chamber 70 is stopped.

On general stoppage of the device by opening the main switch, the solenoid valve 3 will be shifted to the illustrated position so that all of the air under pressure in the first line 200 and the chamber 70 of the mixing device 7 will be exhausted through the port R. This reverse flow back through the nozzle 8 and the filters 6 and 5 as well as the regulator 4 will function to unclog the filters 6 and 5 due to a backwash effect. In addition, the release of the pressure in the chamber 14 causes an opening of the pinch valve 12 to allow a back flow through the nozzle in the second line 10 which will remove any particles and prevent clogging therein. It should be noted that the removal of the air pressure in the vessel or receptacle 70 of the mixing device 7 will not cause any fluidizing of the powder therein. Also, if the valve 12 had pinched the conduit or second line 10 for a short time before deenergizng the system, the majority of the powder entrained in the air of chamber 70 would have settled out. It also can be arranged that the solenoid member 211 of the third control means 11 will also move to the illustratred position which has port A' connected to the exhaust port R' when the main switch of the apparatus is opened.

The circuit of FIG. 2 in spite of its very great simplicity, permits a fluidizing of the powder in the mixing chamber device. It also insures a declogging of the filters and a purge of the exit conduit or second line 10 during a shutdown of the system.

Figure 3:
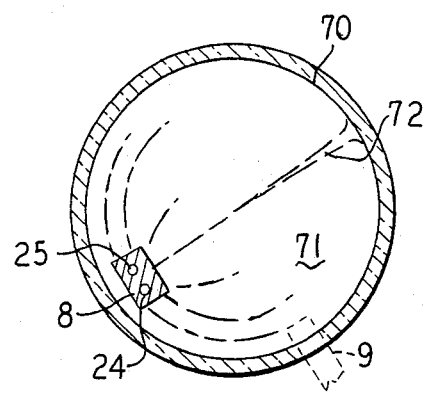
FIG. 3 is a cross-sectional view of the mixing device taken on the lines III—III of FIG. 2.

As illustrated in FIG. 3, the nozzle 8 is a double jet nozzle which preferably has either two parallel jets 24 and 25 or two jets which are either slightly convergent or divergent. The two jets 24 and 25 are directed toward the base of the receptacle 70 with the jets being positioned above the powder level. This permits a simple and effective fluidization of the powder in the chamber 70 by the compressed air jets. The system with the two parallel jets of air also permits a homoegeneous mixing of the entire volume of the receptacle and thus creates a gyrating turbulence permitting both an energetic mixing of the powder when the first air control means 3 is activated by having a voltage placed on the solenoid valve by closing the main switch and the second air line 10 is opened. When the second line 10 is not pinched by the pinch valve 12, a constant vaporization of the powder, regardless of the quantity of the powder, will be created by the jets of the nozzle 8 which create a vertical and vortex turbulence. As best illustrated in FIG. 3, the two jet orifices 24 and 25 of the nozzle 8 are provided in a solid member and are disposed in the proximity of the lateral wall of the receptacle 70 and in an eccentric fashion relative to the axis of the receptacle. As mentioned hereinabove, the terminal part of the nozzle 8 is situated above the level of the powder 71 and brings about an efficient mixing of the powder which mixes efficiently with the compressed air before escaping through an orifice 9 which is advantageously disposed in the upper part of the receptacle and is displaced by approximately 90° as illustrated in broken lines in FIG. 3 from the nozzle 8.

During the entire operation of the mixer device 7, nearly the same dispersion of the powder per unit of volume air will exist whether the receptacle 70 is charged with a high or low level of powder which level remains, however, always lower than the extremity or lower edge of the nozzle 8 or whether the receptacle 70 is almost empty. One thus avoids too strong a concentration of powder at the starting of the apparatus. The fact that the nozzle 8 comprises at least two holes such as 24 and 25 disposed non-axially relative to the receptacle 70 contributes to the creation of two divergent fluxes of mixing directed toward the base of the receptacle 70 and preferably rounded in order that the total fluidization is realized. A zone 72 of the base of the receptacle 70 which is poorly swept by the eddies is virtually negligible. In addition, the position of the orifice 9 is removed from the point of this zone as illustrated in broken lines.

When the solenoid valve of the third control means 11 is positioned to apply pressure to the chamber 14 of the pinch valve 12, the pinch valve will cause a collapse or pinching shut of the second air line or supply conduit 10 which is, for example, composed of a silicone rubber. The pinch valve in combination with the third air control means 11 and the other elements of the pneumatic circuit will enable an automatic purge of the entire system when there is complete stoppage of the apparatus as mentioned hereinabove by the opening of the main switch.

Figure 4:
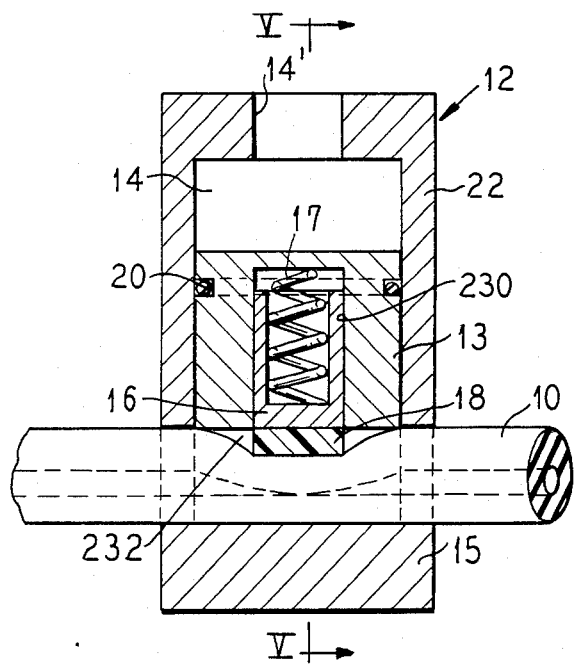
FIG. 4 is a cross-sectional view of a pinch valve taken on the lines IV—IV of FIG. 5.
Figure 5:
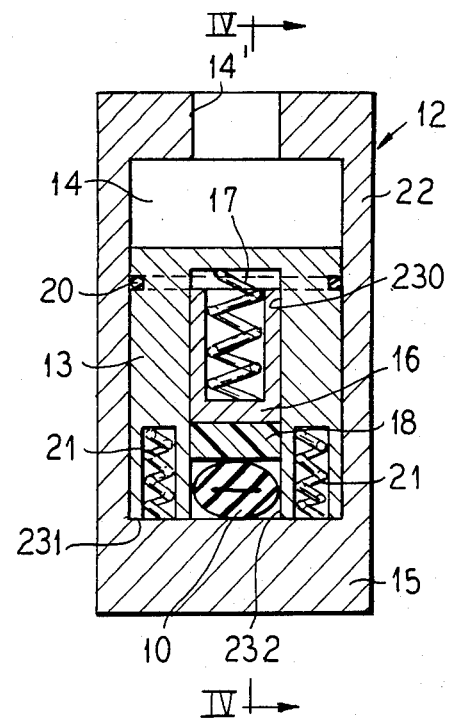
FIG. 5 is a cross-sectional view taken on the lines V—V of FIG. 4.

To insure a selective collapsing of the line 10, the pinch valve 12 preferably has the structure illustrated in FIGS. 4 and 5. As illustrated, the valve 12 has a cylindrical housing 22 with a base 15 at one end and contains a cylindrical chamber 14 that receives a first piston 13. To provide a seal between the walls of the chamber 14 and the piston 13, a toric seal 20 such as an O-ring is provided. The chamber 14 has an outlet 14' which is coupled to a section of the air line 210 to supply air under pressure to the chamber 14. The second air line 10 extends through an opening in the housing 22 adjacent the abutment formed by the end wall or base 15. If the piston 13 was utilized to pinch the tube or air line 10 shut, there is always the problem that an excessive pressure in the chamber 14 will lead to applying too much pressure on the conduit or line 10 to cause deterioration thereof. Another problem would be that the pressure in the chamber 14 might be insufficient to obtain a complete compression or collapse of the tube forming the line 10.

In the preferred embodiment of the pinch valve 12, the first piston 13 is provided with an axial passageway or bore 230 which receives a second piston 16 which is urged toward the base 15 by a spring 17. The piston 13 adjacent the end that engages the base 15 has spring seats for receiving the springs 21 which urge the piston 13 away from the base 15 which acts as an abutment surface or stop. In addition, the piston 13 has a transversely extending passage 232 (FIG. 5) which allows passage of the tube or conduit 10 on the base 15 with engagement by the piston 13. As illustrated, the springs 21 are selected so that the piston 13 will move into contact with the surface abutment surface 15 with a very small fluid pressure being applied in the chamber 14. The actual collapsing or pinching of the tube 10 occurs due to a second piston 16 being urged by the spring 17 against the tube. Preferably, an elastic buffer or pad 18 is provided on the end of the piston 16 to engage the tube 10.

With the construction illustrated in FIGS. 4 and 5, any pressure applied in the chamber 14 will urge the piston 13 to engagement with the abutment surface or stop 15. The spring 17, which acts between the piston 13 and the second piston 16 creates the pressure to insure the collapse or pinching-off of the conduit 10. The force of the spring 17 is the only force that must be taken into account for creating the pressure necessary and sufficient for the collapse of the conduit. Thus, the collapse of the conduit 10 is no longer dependent upon variations in the pressure of the air applied to the chamber 14.

The apparatus 100 as illustrated in FIG. 1 is disposed in a compact fashion in a case or small chest which has a base 106, a front wall 105 and a parallel back wall 104. The back wall 104 as well as the front wall are each provided with guide grooves such as the guide groove 119 of the back wall 104 for guiding and receiving a removable cover or panel 107. In addition, a removable side wall or panel is receivable in grooves such as 120 in the back wall 104 and grooves 121 in the base 106. Inside the case, partitions 108 and 109 create compartments 101, 102 and 103. The cover 107 may have means such as a groove 111 that cooperates with a stop finger 112 mounted on the central partition 109 in order to limit and lock the course or movement of the cover 107. Each compartment contains a part of the elements of the pneumatic circuit of FIG. 2, which elements include a water feeding circuit having a filter, a pressure regulator, a solenoid control valve, a water heater and an electrical feeding element of the apparatus. The front panel or wall is illustrated as having controls 116, 117 and 118 and also a connection for receiving a hose or double conduit 122 of the hand piece 123.

Figure 7:
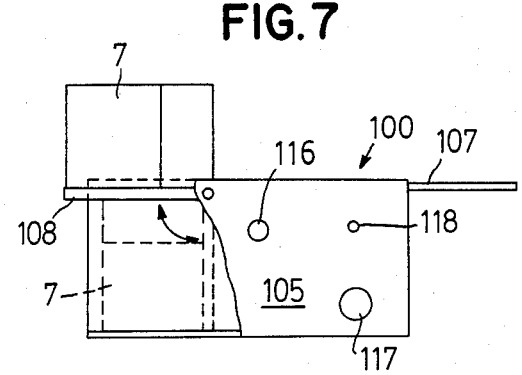
FIG. 7 is a front view of the apparatus with portions broken away showing the partition in a rotated position.

As illustrated in FIG. 1, the mixing device 7 as well as the filters 2, 5 and 6 are all disposed in compartment 103 which is readily accessible because it is limited by a removable lateral wall or side panel which is capable of being readily removed by opening the cover 107. The filters 2, 5 and 6 and the receptacle 70 of the mixing device 7 are preferably mounted on a partition 108 which can be pivoted approximately 90° about its axis (see FIG. 7) in order to bring the elements into a horizontal position which permits a convenient exchange or replacement of these elements. As illustrated, the mixing device 7 has an opening 114 in its upper surface. The cover 107 has an opening 110 which is aligned with the opening 114 so that access to the interior of the mixing receptacle 70 can be obtained even with the cover 107 closed. In order to close the opening 114, a transparent stopper plug or cap 115 which is, for example, formed of an acrylic glass or plexiglass, can be inserted through the opening 110 and screwed into the opening 114 to close the chamber of the device 7. The front panel 105 is illustrated as provided with an opening or cutout portion 113 which enables checking the level of the mixing chamber of the mixing device 7 which receptacle may also be transparent. Thus, the operator can verify that at the time of filling the receptacle the powder charge or layer 71 does not extend to the level of the bottom of the nozzle 8. One should note that although the mixing device 70 is mounted on the rotatable partition 108, the receptacle 70 can be filled in a simple fashion merely by removing the support 115 without rocking or turning or without removing the upper panel 107.

As can be seen in FIG. 1 as well as in FIG. 6, the hand piece 123 comprises a member in the form of a sleeve surrounding a hose or double conduit 122 which has a passage connected to the second line 10 as well as a second passage connected to the water line. The nozzle openings 128 and 129 are formed in a nozzle head 126 which is secured by a rigid conduit 124 to a connector 130 with threads 135 and knurling 136. The connector 130 which is threaded into the sleeve of the hand piece 123 has two rigid conduits 132 and 133 which are of unequal length and are adapted to receive the conduit of the hose 122. The rigid conduit 132 has a shoulder 134 and terminates in a nipple 131. The conduit or connection 133 is in communication with the rigid conduit 124 and is preferably designed for conveying water to the annular first opening 129 which is concentrically arranged to the central second opening 128. It should be noted that the purpose of having different lengths for the conduits 132 and 133 is to prevent interchanging of the connection of the air and water conduits. The centrally disposed second opening 128 is in communication with a nipple 127 which is connected by a flexible tube 125 to the nipple 131. Thus, air charged with the powder is ejected through the central opening 128 of the nozzle 26 to form the jet of air and particles while water passes through the rigid conduit 124 to a chamber which is in communication with the annular first opening 129 to form an annular curtain or screen of water surrounding the centrally disposed jet of air and particles.

Although various minor modifications may be suggested by those versed in the art, it should be understood that I wish to embody within the scope of the patent granted hereon, all such modifications as reasonably and properly come within the scope of my contribution to the art.

I claim:

1. A prophylactic apparatus for cleaning teeth with a flow of air containing powder particles, said apparatus comprising a hand piece with a first nozzle opening and a second nozzle opening, a water line with a valve means extending from a source of water and being connected to the first nozzle opening, a first air line extending from a source of pressurized air to a mixing device, first control means disposed in said first air line for controlling flow of air therethrough, said first air line between the first control means and the mixing device having a section containing at least one air filter, said mixing device having a chamber for receiving powder to be fluidized and mixed with air to form air laden with powder particles, said mixing device having a nozzle connected to the first air line being disposed in the chamber above the level of powder therein and a discharge opening disposed above the level of powder in the chamber connected to a second air line extending to the second nozzle opening of the hand piece, second control means for controlling the flow of air laden with powder particles in said second air line and means for unclogging each filter by creating a reverse flow of air through the chamber, the jet nozzle, the section of the first line and through each filter.

2. A prophylactic apparatus according to claim 1, wherein the first control means and the means for unclogging are formed by a solenoid valve having a valve member movable from a position directly connecting the source of pressurized air to the section of the first air line passing through the filters and a second position with the section of the first air line and filters being vented to the atmosphere.

3. A prophylactic apparatus according to claim 2, which includes a pressure regulator disposed in the first line between the first control means and said filters.

4. A prophylactic apparatus according to claim 2, wherein the second control means comprises a pinch valve being actuated by application of a fluid under pressure and a third control means for controlling the application of fluid to said pinch valve.

5. A prophylactic apparatus according to claim 4, wherein the third control means comprises a solenoid valve having a housing with a first port connected by an air line to the first air line between the section with the filter and the first control means, a second port connected by an air line to the pinch valve and a third port vented to the atmosphere, said solenoid valve having a valve member movable between a position interconnecting the first port to the second port and a second position interconnecting the second port to the third port to vent the control fluid of the pinch valve to the atmosphere.

6. A prophylactic apparatus according to claim 1, wherein the jet nozzle of the mixing device has two vertically directed passageways to create two jets of air in said chamber to fluidize the powder therein.

7. A prophylactic apparatus according to claim 6, wherein the jet nozzle is disposed approximately at a lateral wall of the chamber and eccentric relative to the axis thereof.

8. A prophylactic apparatus according to claim 7, wherein the discharge opening is disposed in the upper portion of the chamber approximately 90° from the location of the jet nozzle.

9. A prophylactic apparatus according to claim 1, wherein the second control means includes a pinch valve having a piston received in a chamber, means for applying a fluid under pressure to said chamber to urge the piston against a stop, said piston carrying an intermediate member engaging the second air line and means biasing the intermediate member from the piston so that variations in the pressure acting on said piston do not affect the pinching and closing of the second air line by the intermediate member.

10. A prophylactic apparatus according to claim 1, wherein the second means for controlling flow through the second line includes a pinch valve having a housing with a cylindrical chamber with a base at one end containing a first piston, spring means biasing the first piston away from said base, said second air line being disposed on said base, said piston having a bore slidably receiving a second piston, spring means biasing the second piston away from said first piston and toward said base to pinch shut the second air line, abutment means for limiting movement of the first piston toward said base and means for applying a control fluid to said chamber to urge said first piston toward said abutment means.

11. A prophylactic apparatus according to claim 10, wherein the second spring means are constructed to exert the necessary pressure to collapse the second air line when the first piston is urged against said abutment.

12. A prophylactic apparatus according to claim 10, wherein said abutment comprises said base and said first piston has a transverse groove for receiving the second air line without engagement therewith.

13. A prophylactic apparatus according to claim 1, wherein the first and second nozzle openings are disposed in a nozzle head with the first nozzle opening being an annular opening concentric to the second opening to provide an annular water curtain around the jet of air and powder issuing from the second opening.

14. A prophylactic apparatus according to claim 1, which includes a case receiving the first and second control means, the filter, the mixing device, said case having an opening in an upper panel to enable removing a stopper from the chamber of the mixing device to enable loading said mixing device.

15. A prophylactic apparatus according to claim 14, wherein the interior of the case is subdivided by at least one partition, said one partition being mounted for pivotal movement in said case, the upper panel of said case being retractible to enable access to the interior of the case, and at least the filter and the mixing device being secured to said one partition so they may be pivoted to gain easy access.

16. A valve for closing a collapsible conduit comprising a housing having a cylindrical chamber with a base at one end for receiving the collapsible conduit, a first piston slidably received in said chamber, spring means biasing the piston away from said base, means for applying a fluid pressure in said chamber to urge said piston toward said base against an abutment limiting movement of the piston toward the base, an intermediate member carried by said piston, spring means for biasing the intermediate member away from the first piston toward said base so that when the first piston is engaging the abutment, said intermediate member pinches the conduit closed.

17. A valve according to claim 16, wherein said intermediate member comprises a second piston slidably received in a bore of the first piston.

18. A valve according to claim 17, wherein the abutment in the base and said first piston has a transverse groove intersecting the path of the second piston on the surface contacting said base to receive the conduit without engagement by said first piston.

* * * * *